United States Patent [19]

Bockman et al.

[11] Patent Number: 4,704,277

[45] Date of Patent: * Nov. 3, 1987

[54] METHODS OF TREATING BONE DISORDERS

[75] Inventors: Richard S. Bockman; Raymond P. Warrell, Jr., both of New York, N.Y.

[73] Assignee: Sloan-Kettering Institute for Cancer Research, New York, N.Y.

[*] Notice: The portion of the term of this patent subsequent to Jul. 16, 2002 has been disclaimed.

[21] Appl. No.: 729,057

[22] Filed: Apr. 30, 1985

[51] Int. Cl.$^4$ .............................................. A61F 33/24
[52] U.S. Cl. ..................................... 424/131; 514/492
[58] Field of Search ................. 424/127, 131; 514/492

[56] References Cited

U.S. PATENT DOCUMENTS 4,529,593 7/1985 Warrell et al. ...................... 424/127

OTHER PUBLICATIONS

Merck Index, 9th ed., pp. 560-561, (1926).

Primary Examiner—Leonard Schenkman
Attorney, Agent, or Firm—John P. White

[57] ABSTRACT

Metal containing compounds have been found which increase bone growth, decrease hydroxyapatite solubility, increase the size and/or the perfection of hydroxyapatite crystals in bone, and increase the tensile strength of bone. These compounds, when administered to patients who are suffering from diseases characterized by bone resorption impede the flow of bone calcium into the blood, and encourage the growth of new, normal bone tissue.

13 Claims, 1 Drawing Figure

METHODS OF TREATING BONE DISORDERS

FIELD OF THE INVENTION

This invention relates generally to disorders associated with bone tissue. In particular, it relates to those disorders which are associated with accelerated resorption of bone, increased calcium levels in the blood, and disordered hydroxyapatite crystal formation and solubility, all of which lead to decreased calcium content in bone, which in turn leads to decreased bone strength, as well as skeletal dysfunction.

PRIOR ART

Applicants' copending U.S. application Ser. No. 622,726 discloses and claims methods of preventing excessive loss of calcium from human bone by administration of pharmaceutically acceptable gallium compounds. Warrell, et al., J. Clin. Invest. 73:1487-1490 (May 1984), disclose the effect of gallium nitrate on calcium resorption in patients with cancer-related hypercalcemia. Warrell, et al., Cancer 51:1982-1987 (June 1983), and Leyland-Jones, et al., in Cancer Treatment Reports 67, No. 10, 941-942 (October 1983), disclose a safe and non-toxic means for administration of gallium nitrate by continuous infusion.

Several agents have been tested for their ability to inhibit bone resorption and affect bone mineral content. Agents which have been tested to date include calcitonin, diphosphonates, fluoride-containing compounds, and vitamin D and its analogs. The natural hormone calcitonin, which must be injected parenterally, can cause a transient decrease in the rate of bone resorption. Repetitive injections have recently been reported to increase bone mineral content as measured by bone densimetric studies, Gruber, et al., Metabolism 33:295-303 (1984). However, the effect on bone resorption is short-lived; escape ("tachyphylaxis") from this anti-resorptive effect occurs rapidly. Moreover, it is not established that the increased bone density seen in studies using calcitonin is a result of increased calcium content. Diphosphonates are another class of compounds which inhibit bone resorption. However, the only pharmaceutically approved diphosphonate (EHDP) blocks normal bone mineralization and leads to formation of disordered and inadequately calcified bone (osteomalacia), Schenk, et al. Calcified Tissue Research 11:196-214 (1973). Of the other diphosphonates, the most potent inhibitor of bone resorption (dichloromethylenediphosphonate) has been removed from clinical testing because of its association with an increased development of leukemia in patients treated with this drug.

Fluoride-containing compounds decrease the incidence of fractures in post-menopausal women with osteoporosis. However, fluoride causes the formation of highly abnormal (lamellar-type) bone structure which is less strong relative to normal bone, Jowsey, et al., Journal of Clinical Endocrinology 28:869 (1968).

All biologically active analogs of vitamin D cause *increased* bone resorption in vitro. Treatment with certain vitamin D analogs has been reported to decrease the incidence of fracture in patients with several bone disorders. However, these analogs do not directly block bone resorption not do they have direct effects on bone calcium content or crystalline structure. In addition, these analogs can cause ectopic calcification and hypercalcemia, both of which are potentially life-threatening disorders.

There is no disclosure or suggestion in the prior art, however, that a pharmaceutically acceptable compound can both increase calcium accretion in bone and decrease bone resorption. Additionally, there are no reports on the effect of administering effective amounts of a pharmaceutically acceptable compound on increasing size or perfection of hydroxyapatite crystals or increasing bone strength.

BACKGROUND

Bone tissue, or bone mass, contains high concentrations of calcium, usually in the form of hydroxyapatite, i.e., $Ca_{10}(PO_4)_6(OH)_2$. The hydroxyapatite is a finely divided, crystalline material which contains contaminating surface ions, such as $CO_3^{2-}$, $Mg^{2+}$, and citrate, which alter its solubility.

Since bone is living tissue, it is constantly being remodelled. Certain bone cells, known as osteoblasts, promote bone formation. Other bone cells, known as osteoclasts, tend to cause bone dissolution. The process of biological calcification is critical in providing the mechanical strength for the skeleton and teeth. Pathological states associated with accelerated loss of bone mineral lead to diseases characterized by skeletal dysfunction and life-threatening metabolic disorders.

Hydroxyapatite, and the calcium of the bone generally exist in equilibrium with body fluids, particularly blood. Although the calcium and hydroxyapatite are soluble in blood, the equilibrium is maintained in healthy individuals, along with a stable and intact bone matrix.

Loss of bone mass from increased bone resorption results in accelerated loss of calcium into the blood. This is a major cause of illness, affecting millions of people in the United States. When significant depletion of bone calcium occurs and the structural integrity of the skeleton is compromised, several diseases result. An example of a diseased state associated with severe loss of bone mass would be osteoporosis, which is a major cause of hip and vertebral fractures in elderly, post-menopausal women. Hypercalcemia, or increased blood calcium concentration, occurs frequently in patients who suffer from hyperparathyroidism or cancer. This hypercalcemia can lead to kidney failure, coma, and death. Bone metastasis, or the spread of cancer cells into bone, occurs in patients who are resistant to cancer therapy, and causes progressive bone erosion, fractures, and excessive pain. All these conditions would be ameliorated by a drug which both decreases bone resorption and increases bone tissue calcium content.

The link between these diseases and the loss of calcium in bone tissue was discovered by investigating the calcium levels of blood and urine of patients who have these diseases. These patients usually had increased levels of blood and urine calcium, when compared to normal individuals. Studies with radiolabeled calcium showed that calcium is resorbed into the blood of patients with the aforementioned diseases at a rate that was much faster than expected.

Clearly, then, there has been a long-standing need for a treatment which would not only prevent resorption of calcium from bone but would also increase the rate of calcium accretion in bone.

It was found that gallium compounds, and gallium nitrate in particular, were effective in reducing excessive loss of bone calcium in humans. This method has been disclosed and claimed in applicants' copending application Ser. No. 622,726, the disclosure of which is incorporated by reference. There was no teaching until the present, however, of accretion of calcium and increased hydroxyapatite crystal formation and/or more perfect hydroxyapatite crystals.

Additional studies have since been undertaken to determine by what mechanism calcium is incorporated into human bone, and how this incorporation may be increased. In the course of these investigations, it has been discovered that various classes of compounds increase normal calcium content in bone tissue and reduce the amount of calcium which is resorbed by the blood. Bone calcification has been found to be increased if the solubility of the hydroxyapatite crystals of bone is reduced. Such an effect was achieved by increasing the size and/or perfection of hydroxyapatite crystals formed in the bone. An increase in the size and/or perfection of the hydroxyapatite crystals reduces their solubility, thereby resulting in this beneficial effect on bone.

It has been found that certain metal containing compounds act on bone tissue to cause increased bone calcium content, to increase the size and/or perfection of hydroxyapatite crystals, and to decrease the solubility of bone hydroxyapatite, all of which lead to increased bone strength. These metallic compounds increase the uptake of calcium by bones and retard the destruction of pre-existing bone tissue as a result of, various disorders, e.g.; metastasis of cancer tumors; hypercalcemia caused by cancer; parathyroid hormone or lymphokine related compounds; or increased bone cell resorbing activity.

Of particular interest in this regard are metal compounds which contain Group IIIa elements, especially gallium compounds such as gallium nitrate. The metallic compounds used have, of course, a low order of toxicity and are pharmaceutically acceptable. They are administered in sufficient dosages to be effective. The effective amount of the particular compound will vary, based upon the nature of the disease being treated, its severity, the age of the patient, and other factors which will be apparent to one skilled in the art.

The following particulars of the invention describe preferred aspects thereof. These particulars, however, should not be taken as limitations to the invention as described, but only of examples of particular, preferred embodiments.

DETAILED DESCRIPTION OF THE PREFERRED EMBODIMENTS

Figure 1:
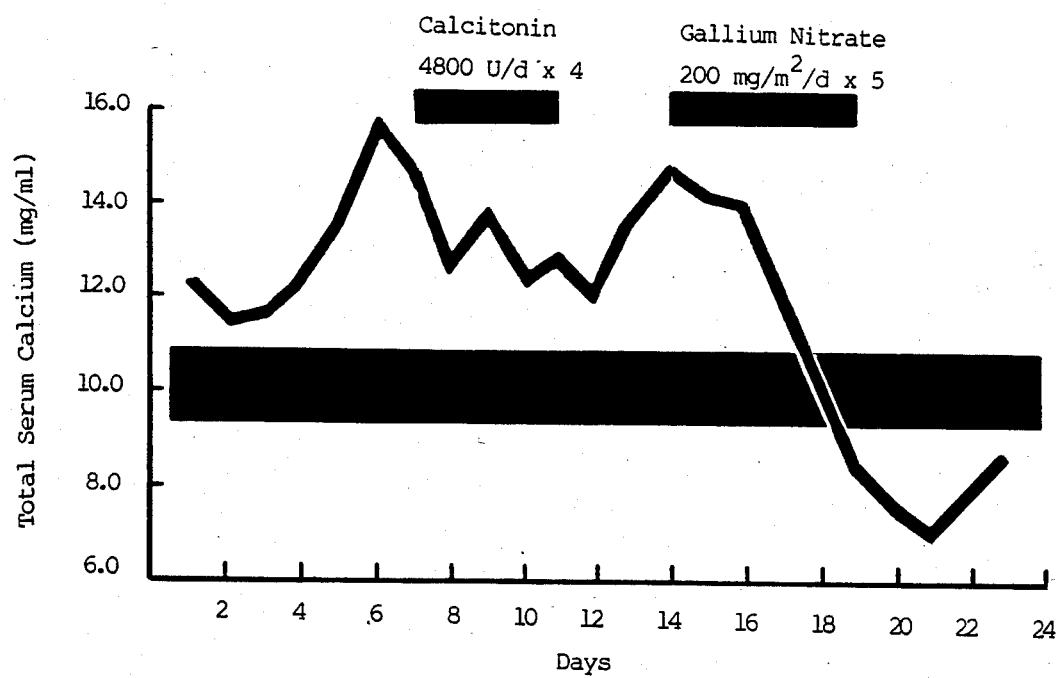
FIG. 1 sets forth, graphically, results of comparative studies as to the effect of calcitonin and gallium nitrate on total serum calcium on a patient with life threatening hypercalcemia.

The following experiments were designed to determine if administration of metallic compounds change bone mineral properties.

Young female (120 g) Sprague-Dawley rats received a course of injections with 0.5 or 5.0 mg gallium nitrate, every other day. The 0.5 mg concentration is approximately equivalent (on a weight/weight basis) to the dose used to treat patients with cancer-related hypercalcemia by Warrell, et. al., supra. The animals received 7 interperitoneal injections over a 9–14 day period. Control groups were injected with carrier only. At the end of the 14 day injection schedule, no differences were noted between the treated and nontreated rats with regard to body weights or weight gained which indicates a lack of toxicity. To obtain bone samples the rats were anesthetized and then sacrificed. The long bones were removed and cleaned of all muscle and connective tissue. The metaphyseal (ends containing the growth plate) and diaphyseal (shaft) portions of the bones were separated using a dissecting microscope. The bone pieces were then split and cleaned of all visible marrow, frozen and lyophilized. The split, dried, marrow-free bone fragments were pulverized in a liquid nitrogen cooled colloid mill to produce bone powder. Aliquots of bone particles were used for: (a) ash weight determination, (b) measurement of Ga, Ca and P content and (c) X-ray diffraction analysis. A portion of one bone particle preparation was sieved to uniform size using an #325 stainless steel mesh. Approximately 50 mg of the sieved-particle bone was then dispersed in bromoform:toluene, density=2.0 g/cc (as measured with a pynconometer). The suspension was centrifuged in the cold at 100 x G for 15 minutes. The suspended particles, representing newly formed mineral bone, density <2.0 g/cc were removed, washed with acetone then dried. The pelleted particles, density >2.0 g/cc were similarly washed with acetone and dried. Both the light and heavy density fractions were analyzed for Ga and Ca content.

Gallium content in bone was measured by flameless atomic absorption spectrophotometry. Inorganic phosphorus was measured spectrophotometrically.

The data on gallium: calcium ratio of the separated and powdered bone fragments from animals receiving different total doses of the agent show that Ga is incorporated into bone in very low amounts. The greatest uptake of gallium was noted in the metaphyseal bone, a region in which active bone turnover is occurring. In subsequent experiments, rats were given 7 injections with 5 mg gallium nitrate over 14 days. Mineral content (ash weights) of the control and gallium treated bones were not significantly different. However, using more sensitive methods, a statistically significant increase in bone calcium content was noted in the metaphyses from the gallium treated compared to the nontreated animals, and shown in Table I. No differences in calcium content were seen between the diaphyseal fragments. Examination of the high and low density fractions separated by bromoform:toluene density centrifugation showed greated Ga content (3.2±0.2 vs. 2.9±0.4 ug Ga/mg Ca) in the lighter bone fraction, <2.0 g/cc which is made up of newly synthesized bone mineral. As expected, increased calcium content was measured in the heavier density fraction >2.0 g/cc (220±31 vs 132±42 ug Ca/mg bone) which contained the more mineralized and more mature hydroxyapatite crystalline material.

Aliquots of the powdered bone were subjected to wide angle x-ray diffraction using Cu K(alpha) radiation. Samples were rapidly scanned from 4° $2\phi$ to 70° $2\phi$ to detect the presence of phases other than hydroxyapatite. Triplicate slow scans from 24° to 28° $2\phi$ were used to estimate hydroxyapatite crystal size and perfection based on the line-width measurements ($B_{002}$) made at the half maximum point of the c-axis 002 reflection at 25.8° $2\phi$. The only phase detected in all samples was hydroxyapatite. As seen in Table I, $B_{002}$ values measured in the metaphyseal derived particles from the gallium-treated animals differed significantly compared to the metaphyses of control rats. Since $B_{002}$ is inversely related to crystal size and/or perfection, the data show that larger or more perfect crystals were present in the region of bone where more active bone mineralization was occurring. As a consequence, crystals formed in the metaphyses of the treated animals were similar to those found in the more mature diaphyses.

TABLE I

Properties of Bone From Gallium-Treated Animals

| (n) - | Ga ng/mg (6) | Ca g/mg (6) | P g/mg (6) | BOO2 degrees (11) |
|---|---|---|---|---|
| Metaphyses: | | | | |
| Gallium Treated = | 384 ± 69 | 372 ± 14 | 178 ± 21 | 0.50 ± .03 |
| Control = | 0 | 341 ± 27 | 166 ± 11 | 0.55 ± .01 |
| Diaphyses: | | | | |
| Gallium Treated = | 149 ± 30 | 356 ± 12 | 173 ± 15 | 0.50 ± .03 |
| Control = | 0 | 356 ± 26 | 171 ± 19 | 0.50 ± .02 |

Additional experiments were then performed, since it had been determined that gallium nitrate directly inhibits bone resorption. These additional experiments were performed to permit evaluation of bone turnover in patients with bone metastases, in response to short term infusion of gallium nitrate.

Seventeen infusions were administered to fifteen patients, five of whom were hypercalcemic. Gallium nitrate was administered as a continuous infusion at daily doses ranging from 100–300 mg/sq mm m/d, over 5–7 days. Bone turnover was assessed by serial measurements of urinary levels of $Ca^{2+}$, hydroxyproline (OHP), and creatinine (Cr), as well as the serum levels of osteocalcin (BGP). The urinary 24 hour $Ca^{2+}$ excretion hours after administration of the drug, was markedly reduced after each infusion in all 15 patients. Mean reduction was 70±18%. Eight patients with increased bone turnover (i.e., a urinary OHP/Cr ratio greater than 6.0), received eleven drug infusions. All patients showed a decrease in OHP/Cr. Mean reduction was 49±22%. Six patients with bone turnover which was not elevated showed no significant change in this ratio. These data show that gallium treatment reduces accelerated bone loss in cancer patients with bone matastases.

Cytotoxicity studies were undertaken to determine if gallium nitrate was cytotoxic to bone tissue. Histological studies show no evidence of cytotoxic effect at the light microscopic level. Additionally, stained sections show no alteration in matrix or mineral components. Little change in cell numbers or viability was seen when bone cell models were treated for 48 hours with up to 25 uM of gallium nitrate. At this dose and time, a 20% decrease in $^3H$-thymidine incorporation into DNA was seen. If gallium treated and untreated cells were labeled with $^3H$-amino acids, no differences were seen in the protein banding patterns on the SDS-PAGE gels of the cell homogenates.

These results show that the action of gallium is not a consequence of a cytotoxic effect on bone cells.

Comparative studies were performed as to the effect of Calcitonin on total serum calcium, compared to gallium nitrate in a patient with severe life-threatening hypercalcemia due to bone metastases. These results are summarized in FIG. 1, normal range of $Ca^2+$ is indicated by the shaded block. Even though the amount of calcitonin used was many times over the recommended dose for treatment, gallium nitrate had a distinctly greater effect on reducing elevated serum calcium, again indicating a reversal of bone resorption.

One skilled in the art will immediately see the applicability of these preferred embodiments to other compounds and situations. For example, gallium is a member of the group IIIa metals, with properties similar to those other members of the group. Hence, one skilled in the art would expect metal compounds which contain metal similar to gallium would be effective also. Additionally, one would expect the compositions and methods described herein to be applicable to similar tissues. Human bone is similar, in may respects to bone of other animals; hence the veterinary applications of this invention are clear. Similarly, the calcium in bones surrounding teeth makes it clear that this invention is applicable, e.g., to periodontal disease treatment.

The link between increased bone calcium content and bone strength has been attested to, and one skilled in the art will therefore see that the compositions and methods disclosed herein may be used to increase bone strength.

In the practice of this invention, any of the standard ways of administering compositions to patients may be employed, including, but not limited to, concentrated rinses, gels, intravenous injection, including continuous infusion, oral, sublingual, rectal, or transdermal administration. In a preferred form of the invention using gallium nitrate, intravenous injection supplies about 10–400 mg/sq mm/day to patients. Another preferred embodiment maintains a range of about 0.1–5.0 ug/ml of compound at a steady state in the plasma, and, even more preferably, about 0.5–2.0 ug/ml. When administered orally, sublingually, rectally or transdermally, the compounds are administered in amounts ranging from about 0.5–20 grams/day.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method of increasing calcium accretion in bone tissue and decreasing bone resorption comprising administering to a subject with a calcium accretion and bone resorption disorder a pharmaceutically acceptable gallium containing composition selected from the group consisting of gallium nitrate, gallium citrate, gallium chloride, gallium carbonate, gallium acetate, gallium tartrate, gallium oxalate, gallium oxide, and hydrated gallium oxide, wherein said compositions are useful in increasing calcium content of bone tissue and decreasing bone resorption, in an amount sufficient to cause an increase in calcium content of said bone and to cause decreased bone resorption.

2. A method as in claim 1, wherein said compound is gallium nitrate.

3. A method as in claim 1, wherein said compound is administered intra-orally in a topical formulation comprising a concentrated rinse, gel, or other pharmaceutically acceptable carrier.

4. A method as in claim 1, wherein said compound is administered intravenously, subcutaneously, or intramuscularly.

5. A method as in claim 1, wherein said compound is administered by continuous intravenous infusion.

6. A method of claim 1, wherein said compound is administered by intravenous injection comprising an amount ranging from about 10–400 mg/sq mm/day.

7. A method as in claim 1, wherein said compound is administered in an amount sufficient to maintain a steady state plasma concentration of said compound ranging from about 0.1–5.0 ug/ml.

8. A method as in claim 1, wherein said compound is administered in an amount sufficient to maintain a steady state plasma concentration from about 0.5–2.0 ug/ml.

9. A method as in claim 1, wherein said compound is administered orally, sublingually, per rectum or transdermally.

10. A method as in claim 1, wherein said compound is administered orally, sublingually, per rectum or transdermally in an amount ranging from about 0.5–20 grams/day.

11. A method as in claim 1, wherein an amount of said composition sufficient to increase bone crystal growth is administered to said subject.

12. A method as in claim 1, wherein an amount of said composition sufficient to decrease hydroxyapatite solubility is administered to said subject.

13. A method as in claim 1, wherein an amount of said composition sufficient to increase size and/or perfection of hydroxyapatite crystals in bone tissue is administered to said subject.

* * * * *